United States Patent [19]

Della Bella et al.

[11] Patent Number: 4,952,596
[45] Date of Patent: * Aug. 28, 1990

[54] DERIVATIVES OF THIAZOLIDINE-4-CARBOXYLIC ACID HAVING PHARMACOLOGICAL ACTIVITY

[75] Inventors: Davide Della Bella, Milan; Angelo Carenzi, Busto Arsizio; Dario Chiarino, Monza; Franco Pellacini, Sesto San Giovanni, all of Italy

[73] Assignee: Zambon S.p.A., Vicenza, Italy

[*] Notice: The portion of the term of this patent subsequent to Jun. 20, 2006 has been disclaimed.

[21] Appl. No.: 287,042

[22] Filed: Dec. 21, 1988

[30] Foreign Application Priority Data

Dec. 21, 1987 [IT] Italy .................. 23126 A/87

[51] Int. Cl.$^5$ .................. C07D 277/06; A61K 31/425
[52] U.S. Cl. .................... 514/365; 514/342; 546/280; 548/181; 548/200; 548/201
[58] Field of Search ............ 548/200, 201, 181; 546/280; 514/365, 342

[56] References Cited

U.S. PATENT DOCUMENTS 4,775,675 10/1988 Gyorgydeck .................. 514/307

Primary Examiner—Robert Gerstl
Attorney, Agent, or Firm—Cushman, Darby & Cushman

[57] ABSTRACT

Compounds of the formula

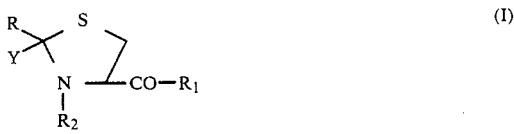

wherien R, $R_1$, $R_2$ and Y have the meanings mentioned in the description, processes for their preparation and their use in the pharmaceutical field are described.

The compounds of formula I are endowed with antipyretic, anti-inflammatory, mucolitic and analgesic activity together with good gastric tolerability.

In addition, the compounds of formula I are active in the treatment of ischemic or reperfusion syndromes.

9 Claims, No Drawings

DERIVATIVES OF THIAZOLIDINE-4-CARBOXYLIC ACID HAVING PHARMACOLOGICAL ACTIVITY

DESCRIPTION

The present invention relates to N-acyl derivatives of thiazolidine-4-carboxylic acid and more particularly to derivatives of N-acyl-thiazolidine-4-carboxylic acid substituted at position 2 and optionally at the carboxylic group and the corresponding salts with pharmaceutically acceptable acids or bases.

The invention also relates to the preparation of such compounds and their use in the pharmaceutical field.

Several thiazolidine-4-carboxylic derivatives substituted at position 2 and having pharmaceutical activity are known.

Among these one may mention the compounds endowed with anti-tumoral activity described in the Japanese patent application No. 82/128,625 (Chemical Abstracts, 97:203231b) in the name of Kaken Chemical Co., in which at the position 2 of the thiazolidine ring there is an alkyl, a phenyl, a naphthyl or a benzyl group and the compounds having bacteriostatic and fungistatic activity described in the German patent application No. 2,208,533 (Chemical Abstract, 80:3529s) in the name of Kolmar Laboratories Inc., in which at the position 2 there is an n-undecyl or a benzyl group.

The said compounds have a free or salified carboxylic group at position 4.

An object of the present invention are the compounds of the formula

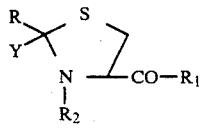

(I)

wherein
Y is hydrogen or methyl; when Y=H
R is a radical selected from:
(6-methoxy-2-naphthyl)-methyl,
1-(4-isobutylphenyl)-ethyl,
1-(6-methoxy-2-naphthyl)-ethyl,
5-(2,4-difluorophenyl)-2-hydroxyphenyl,
2-(3-trifluoromethyl-phenylamino)-phenyl,
(Z)-5-fluoro-2-methyl-1-(4-methylsulfinylbenzylidene)-1H-inden-3-yl-methyl,
1-(4-chlorobenzoyl)-5-methoxy-2-methyl-1H-indol-3-yl-methyl,
1-(3-benzoyl-phenyl)-ethyl,
2(2,6-dichlorophenylamino)-benzyl,
1-[4-(2-thienyl-carbonyl)-phenyl]-ethyl
when Y=CH$_3$
R is 2-(6-methoxy-2-naphthyl)-ethyl;
R$_1$ is hydroxy, C$_1$-C$_6$ alkoxy, amino, mono- or dialkylamino wherein the alkyl has from 1 to 4 carbon atoms, a radical of an aminoacid of the formula

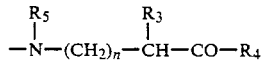

wherein
R$_5$ is hydrogen;

R$_3$ is hydrogen, C$_1$-C$_4$ alkyl, optionally substituted by hydroxy, SH, SCH$_3$, or a phenyl optionally substituted by 1 or 2 hydroxy groups;
n is an integer chosen from 0, 1 and 2; when n=0, R$_5$ and R$_3$ together may also form a —(CH$_2$)$_3$— or —CH$_2$—S—CH$_2$— group;
R$_4$ is hydroxy, C$_1$-C$_6$ alkoxy or a radical of an aminoacid of the formula

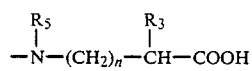

wherein R$_5$, R$_3$ and n have the meanings already mentioned;

R$_2$ is an acyl radical of a saturated or unsaturated aliphatic monocarboxylic acid, an aromatic or an arylaliphatic acid having up to 16 carbon atoms, of a heterocyclic monocarboxylic acid having a ring with 5 or 6 members containing 1 or 2 heteroatoms chosen from nitrogen, oxygen or sulphur, or of an aliphatic or aromatic bicarboxylic acid having up to 12 carbon atoms;

and their salts with pharmaceutically acceptable acids or bases.

R$_2$ is preferably an acyl radical of the following carboxylic acids:

(a) pharmaceutically acceptable monocarboxylic acids selected, for example, among acetic, propionic, butyric, isobutyric, pentanoic, hexanoic, tertbutylacetic, octanoic, decanoic, lauric, lactic, palmitic, thiolactic, pivalic, phenylacetic, phenoxyacetic, glyceric, 2-phenylpropionic, benzoic, 3,5-dimethylbenzoic, cinnamic, sorbic, 2- or 4-hydroxybenzoic, 4-aminosalicylic, 5-bromo-acetylsalicyclic, 2,5-dihydroxybenzoic, 4-methoxybenzoic, acetylsalicyclic, betamercapto-propionic, 4-acetoxy-benzoic acnd 4-acetamidobenzoic acid;

(b) pharmaceutically acceptable bicarboxylic acids selected, for example, among tartaric, citric, succinic, malic, phthalic and hydroxyphthalic acid wherein the free carboxylic group is optionally salified by a pharmaceutically acceptable organic or inorganic base;

(c) pharmaceutically acceptable heterocyclic acids selected, for example, among 2-pyridine-carboxylic, 3-pyridine-carboxylic and 4-pyridine-carboxylic acid.

The compound of formula I are endowed with anti-pyretic, anti-inflammatory, mucolitic and analgesic activity and, moreover, they are active in the treatment of ischemic pathologies and in pathologies caused by overproduction of oxidant radicals.

The compounds of formula I may be prepared by acylation of the corresponding thiazolidine-4-carboxylic derivatives of the formula

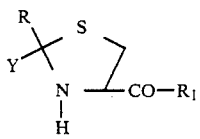

(II)

wherein R, R$_1$ and Y have the meanings already mentioned in connection with formula I; described in the EP-A- No. 0 254 354 in the name of Zambon S.p.A..

The acylation step is performed by treatment of a compound of formula II with a suitable acylating agent in an inert organic solvent, optionally in the presence of an inorganic base such as an alkali carbonate or bicarbonate or of an organic base such as triethylamine.

Examples of suitable acylating agents are the carboxylic acids and the acyl reactive derivatives such as the acyl halides and anhydrides. Examples of suitable solvents are methylene chloride, chloroform, tetrahydrofurane, 1,2-dichloroethane, ethyl acetate, 1,4-dioxane.

As an alternative, when preparing the compounds of formula I wherein $R_1$ is $-M(R_5)-(CH_2)_n-CH(R_3)-COR_4$, the acylation reaction may be performed on the corresponding compound of formula II wherein $R=OH$.

The thus obtained N-acylated compound ($I-R_1=OH$) is then condensed with an aminoacid or a dipeptide of the formula

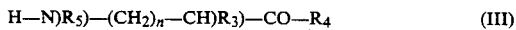
$$H-N(R_5)-(CH_2)_n-CH(R_3)-CO-R_4 \quad (III)$$

wherein $R_3$, $R_4$, $R_5$ and n have the meanings already mentioned.

This condensation is carried out according to techniques known in the peptides chemistry, for example in the presence of a suitable condensing agent such as dicyclohexylcarbodiimide and N-hydroxybenzotriazole.

The compound of formula III are aminoacids or esters thereof ($R_4=OH$, alkoxy) or dipeptides [$R_4=N(R_5)-(CH_2)_n-CH(R_3)-COOH$] which are known or can be easily prepared according to known methods, for example by condensation of two aminoacids suitably protected in the presence of dicyclohexylcarbodiimide and N-hydroxybenzotraizole.

The compound of formula II may be prepared (as described in the above-mentioned EP-A-No. 0 254 354 Zambon S.p.A.), by reaction of a carbonyl compound of the formula

$$\begin{array}{c} Y \\ | \\ R-C=O \end{array} \quad (IV)$$

with cysteine.

The carbonyl compounds of formula IV are known compounds or they may be easily prepared by reduction, according to conventional methods, of the corresponding carboxylic acids of the formula

$$R-COOH \quad (V)$$

when $Y=H$ or by oxidation of the corresponding alcohols of the formula

$$\begin{array}{c} Y \\ | \\ R-CH-OH \end{array} \quad (VI)$$

The carboxylic acids of formula V are known, pharmaceutically active compounds endowed with anti-pyretic, anti-inflammatory and analgesic activity.

They are known by the following common names:
Ibuprofen [R=1-(4-isobutylphenyl)-ethyl],
Naproxen [R=1-(S)-(6-methoxy-2-naphthyl)-ethyl],
Diflunisal [R=5-(2,4-difluorophenyl)-2-hydroxy-phenyl],
Flufenamic acid [R=2-(3-trifluoromethyl-phenylamino)-phenyl],
Sulindac [R=(Z)-5-fluoro-2-methyl-1-(4-methylsulfinyl-benzylidene)-1H-inden-3-yl-methyl],
Indometacin [R=1-(4-chlorobenzoyl)-5-methoxy-2-methyl-1H-indol-3-yl-methyl],
Ketoprofen [R=1-(3-benzoyl-phenyl)-ethyl],
Diclofenac [R=2-(2,6-dichlorophenylamino)-benzyl],
Suprofen {R=1-[4-(thienylcarbonyl)-phenyl]-ethyl}.

Among the compounds IV Nabumetone [4-(6-methoxy-2-naphthyl)-butan-2-one] is a known drug endowed with anti-inflammatory and analgesic activity.

The compounds of the present invention have several asymmetry centers. Typical asymmetry centers are the carbon atoms on position 2 and 4 in the thizolidine ring and the carbon atoms of the R substituent which is at alpha-position to the thiazolidine ring when R is a radical chosen from
1-(4-isobutylphenyl)-ethyl,
1-(6-methoxy-2-naphthyl)-ethyl,
1-(3-benozyl-phenyl)-ethyl, and
1-[4-(2-thienylcarbonyl)-phenyl]-ethyl.

By suitably selecting the compounds of formula II used in the synthesis of the compounds of formula I it is possible to prepare the compounds of formula I having the desired optical isomerism.

In particular the configuration of the carbon atom at the position 4 of the thizolidine ring depends on the R or S configuration of the cysteine used in the preparation of the compounds of formula II. Likewise, the configuration of the carbon atom at alpha to position 2 of the thiozolidine ring depends on the R or S configuration of the carbon atom at alpha to the carbonyl group in the compounds of formula IV.

The pharmaceutically acceptable salts of the compounds of formula I may be prepared by usual methods.

The salts with bases are obtained by salification of the carboxylic group on the position 4 of the thiazolidine ring ($R_1=OH$) or of the free carboxylic group when $R_2$ is an acyl from a bicarboxylic acid or also by salification of carboxylic groups optionally present on the $R_1$ substituent or of other acid functions optionally present on the $R_2$ substituent.

Typical examples of pharmaceutically acceptable bases are the alkali and earth-alkaline metals such as Na, K, Ca and Mg, and the organic bases such as 2-aminoethanol, trihydroxymethyl-aminomethane, glucosamine, lysine and arginine.

The salts with acids are obtained by salification of amino groups optionally present on the $R_1$ and $R_2$ substituents. Examples of useful acids are the pharmaceutically acceptable fatty acids and mineral acids.

As mentioned above the compounds of formula I are endowed with valuable pharmacological properties.

They, in fact, are endowed with anti-pyretic, anti-inflammatory, mucolitic and analgesic action.

Compared with the acids of formula V, the compounds of formula I show a similar profile as far as the anti-pyretic, anti-inflammatory and analgesic action is concerned, in terms of both quality and quantity.

A salient difference is indeed the gastric tolerability which is a serious drawback of many acids of formula V but which is very good for the compounds of the present invention.

In addition, the compounds of the present invention proved to be active as mucolytics and in the treatment of ischemic and reperfusion syndromes (M. Bernier et al., Circulation Research, 58 331–340, 1986) concerning various tissues and parenchymas (for example, by preventing reperfusion and reinfarction arrythmias) and in the treatment of parenchymal alterations due to an overproduction of oxidant radicals by endogenous and esogenous factors.

The compounds of the present invention proved to be endowed with preventive action on GSH depletion (reduced glutathione).

Peculiar and innovative proved to be also the ability of the compounds of formula I in preventing arrythmias from reperfusion in the post-infarctual and reinfarctual syndromes.

Once the acute phase of infraction has been overcome, the patient, during reperfusion, aided by spontaneous or pharmaceutically-induced thrombolysis or by-pass operations, runs a serious risk of arrythmias (ectopic beats, tachycardia and ventricular fibrillation) which in many cases can prove fatal.

Since the compounds of formula I proved to be well tolerated both by oral route and by endovenous injection, they can therefore be used in human therapy as anti-pyretic, anti-inflammatory, mucolitic and analgesic drugs but most of all as drugs capable of preventing the oxidative injuries and the reperfusion damages in the post-infarction and reinfarction syndrome and also in the ischemic and post-ischemic syndromes, and the injuries by oxidant radicals at the pulmonar, cerebral and intestinal levels.

The compounds of the present invention may be administered by oral or rectal routes at doses of from 200 to 4,000 mg/day and by the intravenous route at doses of from 100 to 2,000 mg/day.

For therapeutical purposes the compounds of formula I are preferably incorporated into pharmaceutical dosage forms suitable for the desired administration route such as tablets, dragees, capsules, granules, suppositories, solutions, suspensions and lyophilized compositions to be diluted to obtain injectable liquids.

Such pharmaceutical dosage forms are prepared by conventional techniques and, in addition to the selected compound of formula I, they contain solid or liquid inert diluents and carriers and pharmaceutically useful additives such as aggregants, disaggregants, salts for regulating the osmotic pressure, buffers, sweeteners and colouring agents.

Particularly useful in preventing the reinfarction are also slow-release pharmaceutical forms for oral use which are prepared according to conventional techniques.

For the purpose of better illustrating the present invention, without limiting it in any way, the following examples are now given.

EXAMPLE 1

3-acetyl-2-[(1R)-1-(4-isobutylphenyl)-ethyl]-thiazolidine-4(R)-carboxylic acid

To a suspension of 2-[(1R)-1-(4-isobutylphenyl)-ethyl]-thiazolidine-4(R)-carboxylic acid (3 g; 0.010 mol) in tetrahydrofuran (5 ml) a solution of NaHCO$_3$ (3 g) in water (50 ml) is slowly added.

To the thus obtained solution, kept under stirring at room temperature, acetic anhydride (2.13 ml; 0.021 mol) is added dropwise.

After two hours, ethyl acetate (50 ml) is added.

The organic phase is separated. The aqueous phase is acidified with hydrochloric acid and extracted with ethyl acetate.

After drying on sodium sulphate and evaporation of the solvent a crude product is obtained (3.7 g) which is purified by chromatography on silica gel eluenting with methylene chloride:ethyl acetate:acetic acid=6:4:1, yielding 3-acetyl-2-[(1R)-1-(4-isobutylphenyl)-ethyl]-thiazolidine-4(R)-carboxylic acid (2.4 g) as a solid which is crystallized from terbutyl-methyl-ether.

m.p.=150°–153° C.

$[\alpha]_D^{20}=-64.5°$ C. (c=1, DMF)

$^1$H-NMR (200 MHz, CDCl$_3$): delta (ppm): 0.88 [d, 6H, (CH$_3$)$_2$CH, J=4.9 Hz]; 1.35 (d, 3H, CH$_3$—CH, J=7.1 Hz); 1.84 [m, 1H, (CH$_3$)$_2$CH]; 2.26 (s, 3H, CH$_3$CO); 2.44 (d, 2H, PhCH$_2$, J=7.2 Hz); 3.05 (dq, 1H, CH$_3$CH); 3.20 (dd, 1H, H$_B$—C—S, J$_{AB}$=12.4 Hz, J$_{BX}$=8.8 Hz); 3.55 (dd, 1H, H$_A$—C—S, J$_{AB}$=12.4 Hz, J$_{AX}$=8.9 Hz); 4,95 (dd, 1H, H$_X$—C—COO, J$_{AX}$=8.9 Hz, J$_{BX}$=8.8 Hz); 5.07 (d, 1H, S—CH—N, J=8.8 Hz); 7.11 (s, 4H, aromatics).

EXAMPLE 2

3-acetyl-2-[(pb 1S)-1-(4-isobutylphenyl)-ethyl-thiazolidine-4(R)-carboxylic acid Working as described in Example 1 and using 2-[(1S)-1-(4-isobutylphenyl)-ethyl]-thiazolidine-4(R)-carboxylic acid (10 g; 0.034 mol) as the starting product, a crude product (10.3 g) is obtained which is crystallized twice from isopropyl ether until a pure product (7.1 g; yield 62%) is obtained. m.p.=131°–133° C.

$[\alpha]_D^{20}=210.8°$ C. (c=1, DMF)

$^1$H-NMR (200 MHz, CDCl$_3$): delta (ppm): 0.85 [d, 6H, (CH$_3$)$_2$CH]; 1.42 (s, 3H, CH$_3$—CO); 1.45 [d, 3H, (CH$_3$)CH, J=7.1 Hz]; 1.81 [m, 1H, (CH$_3$)CH$_2$CH]; 2.42 (d, 2H, PhCH$_2$, J=7.1 Hz); 2.90 (dq, 1H, CH$_3$—CH—Ph); 3.27 (dd, 1H, S—CH$_B$—CH$_X$, J$_{AB}$=12.6 Hz, J$_{BX}$=8.9 Hz); 3.91 (dd, 1H, S—CH$_A$—CH$_X$, J$_{AB}$=12.6 Hz, J$_{AX}$=8.4 Hz); 4.8 (d, 1H, Ph—CH—CH, J=10.2 Hz); 4.88 (dd, 1H, S—CH$_2$—CH$_X$, J$_{AX}$=8.4 Hz, J$_{BX}$=8.9 Hz); 7.10 (s, 4H, aromatics).

EXAMPLE 3

N-{3-acetyl-2-[(1S)-1-(4-isobutylphenyl-ethyl]-thiazolidine-4(R)-carbonyl}-beta-alanine ethyl ester To a solution of N-{2-[(1S)-1-(4-isobutylphenyl)-ethyl]-thiazolidine-4(R)-carbonyl}-beta-alanine ethyl ester hydrochloride (2 g; 0.0046 mol) in methylene chloride (30 ml), triethylamine (13 ml; 0.0094 ml) is added under stirring and at 0° C. and, after that, acetyl chloride (0.34 g; 0.0048 mol).

The temperature of the reaction mixture is allowed to rise to the room temperature and the mixture is then kept under stirring for two hours.

Methylene chloride is evaporated to dryness and the residue is treated with ethyl ether and a 5% solution of hydrochloric acid. The phases are separated and the ethereal phase is washed with a 5% solution of sodium bicarbonate and then with water.

After drying on sodium sulphate and evaporation of the solvent, an oil (1.8 g) is obtained which consists mainly (91%) of the desired product (yield, 72%). An analytically-pure sample is obtained by chromatography on a silica gel column; eluent, methylene chloride:ethyl acetate=6:4.

$[\alpha]_D^{20}=-141.6°$ C. (c=1, DMF).

$^1$H-NMR (200 MHz, DMSO-d$_6$): delta (ppm): 0.84 (d, 3H, CH$_3$—CH—CH$_3$, J=6.6 Hz); 0.86 (d, 3H, CH$_3$—CH—CH$_3$, J=6.6 Hz); 1.29 (t, 3H, CH$_3$CH$_2$O, J=7.1 Hz); 1.40 (s, 3H, CH$_3$CO*); 1.40 (d, 3H, CH$_3$CHPh, J=7.0 Hz); 1.64 (s, 3H, CH$_3$CO*); 1.80 (m, 1H, CH$_3$—CH—CH$_3$); 2.40 (d, 2H, CH$_2$Ph, J=7.3 Hz); 2.50 (m, 2H, CH$_2$COO); 2.95–3.14 (m, 2H, NH—CH$_2$); 3.39–3.76

(m, 2H, S—CH—CH+CH—CH₃); 3.92-4.06 (m, 1H, S—CH—CH); 4.14 (q, 2H, OCH₂, J=7.1 Hz); 4.78 (d, 1H, S—CH—N, J=10.4 Hz); 4.90 (dd, 1H, N—CH—CO); 7.02 (s, 4H, aromatics); 7.62 (m, 1H, NH).

*=the acetamido signal is split into two parts by the presence of sin-anti conformers.

We claim:

1. A compound of the formula

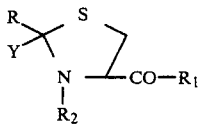
(I)

wherein

Y is hydrogen or methyl; when Y=H
R is a radical chosen from:
(6-methoxy-2-naphthyl)-methyl,
1-(4-isobutylphenyl)-ethyl,
1-(6-methoxy-2-naphthyl)-ethyl,
5-(2,4-difluorophenyl)-2-hydroxyphenyl,
2-(3-trifluoromethyl-phenylamino)-phenyl,
(Z)-5-fluoro-2-methyl-1-(4-methylsulfinylbenzylidene)-1H-inden-3-yl-methyl,
1-(4-chlorobenzoyl)-5-methoxy-2-methyl-1H-indol-3-yl-methyl,
1-(3-benzoyl-phenyl)-ethyl,
2-(2,6-dichlorophenylamino)-benzyl,
1-[4-(2-thienyl-carbonyl)-phenyl]-ethyl, when Y=CH₃
R is 2-(6-methoxy-2-naphthyl)-ethyl;

$R_1$ is hydroxy, $C_1-C_6$ alkoxy, amino, mono- or dialkylamino wherein the alkyl has from 1 to 4 carbon atoms, a radical of an aminoacid of the formula

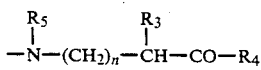

wherein $R_5$ is hydrogen;
$R_3$ is hydrogen, $C_1-C_4$ alkyl, optionally substituted by hydroxy, SH, SCH₃, or a phenyl optionally substituted with 1 or 2 hydroxy groups;
n is an integer chosen from 0, 1 and 2; when n=0, $R_5$ and $R_3$ together may also form a —(CH₂)₃— or —CH₂—S—CH₂— group;
$R_4$ is hydroxy, $C_1-C_6$ alkoxy or a radical of an aminoacid of the formula

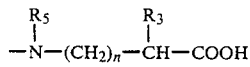

wherein $R_5$, R and n have the meanings already mentioned;

$R_2$ is an acyl radical of:
(a) a pharmaceutically acceptable monocarboxylic acid chosen from acetic, propionic, butyric, isobutyric, pentanoic, hexanoic, tertbutylacetic, octanoic, decanoic, lauric, lactic, palmitic, thiolactic, pivalic, phenylacetic, phenoxyacetic, glyceric, 2-phenylpropionic, benzoic, 3,5-dimethylbenzoic, cinnamic, sorbic, 2- or 4-hydroxybenzoic, 4-aminosalicylic, 5-bromo-acetylsalicylic, 2,5-dihydroxybenzoic, 4-methoxybenzoic, acetylsalicylic, betamercapto-propionic, 4-acetoxybenzoic and 4-acetamidobenzoic acid;
(b) a pharmaceutically acceptable bicarboxylic acid chosen from tartaric, citric, succinic, malic, phthalic and hydroxyphthalic acid wherein the free carboxylic group is optionally salified by a pharmaceutically acceptable organic or inorganic base;
(c) a pharmaceutically acceptable heterocyclic acid selected among 2-pyridinecarboxylic, 3-pyridinecarboxylic and 4-pyridinecarboxylic acid.

2. A compound according to claim 1 wherein R is 1-(4-isobutylphenyl)-ethyl.

3. A compound according to claim 1 wherein R is 1-(6-methoxy-2-naphthyl)-ethyl.

4. A compound according to claim 1 wherein R is 1-(3-benzoylphenyl)-ethyl.

5. A compound according to claim 1 wherein $R_1$ is hydroxy.

6. A compound according to claim 1 wherein $R_1$ is $C_1-C_6$ alkoxy.

7. A compound according to claim 1 in which $R_1$ is hydroxy, in the form of sodium salt.

8. A compound according to claim 1 in which the carbon atom at the position 4 of the thiazolidine ring has configuration R.

9. A pharmaceutical composition comprising a compound according to claim 1 as the active ingredient together with inert solid or liquid carriers or diluents and, optionally, with additives for pharmaceutical use, said compound being present in the composition in an amount effective for treating a patient showing inflammatory and painful conditions, or requiring fluidification of mucus, or for preventing arrhythmias due to reperfusion and reinfarction.

* * * * *